United States Patent [19]

Mamuzic et al.

[11] Patent Number: 4,754,053

[45] Date of Patent: Jun. 28, 1988

[54] PROCESS FOR PREPARING ALKYL TETRABROMOPHTHALATES

[75] Inventors: Rastko I. Mamuzic, West Lafayette; Bhabatosh Bhattacharya, Lafayette, both of Ind.

[73] Assignee: Great Lakes Chemical Corporation, West Lafayette, Ind.

[21] Appl. No.: 48,866

[22] Filed: May 12, 1987

[51] Int. Cl.$^4$ ............................................. C07C 67/48
[52] U.S. Cl. ........................................ 560/78; 560/79; 560/83; 560/99; 562/485; 562/487
[58] Field of Search ...................... 560/78, 79, 83, 99; 562/485, 487

[56] References Cited

U.S. PATENT DOCUMENTS 4,284,793  8/1981  Sagara et al. ........................ 560/78
4,304,925  12/1981  Watanabe et al. .................... 560/78

Primary Examiner—Werren B. Lone
Assistant Examiner—Vera C. Clarke
Attorney, Agent, or Firm—Kirkland & Ellis

[57] ABSTRACT

Bis(2-ethyl-1-hexyl) tetrabromophthalate produced by the reaction of tetrabromophthalic anhydride with 2-ethyl-1-hexanol in the presence of titanium isopropoxide catalyst may be purified by contacting the reaction mixture with sodium carbonate decahydrate with agitation for a time and at a temperature sufficient to enhance product quality, followed by isolation of bis(2-ethyl-1-hexyl) tetrabromophthalate.

14 Claims, No Drawings

PROCESS FOR PREPARING ALKYL TETRABROMOPHTHALATES

BACKGROUND OF THE INVENTION

1. Field of the Invention

This invention relates to the preparation of alkyl tetrabromophthalates produced by the reaction of tetrabromophthalic anhydride with alkanols in the presence of titanium (IV) lower alkoxide catalyst.

2. Description of the Prior Art

The known synthesis of bis(2-ethyl-1-hexyl) tetrabromophthalate involves the reaction of tetrabromophthalic anhydride with 2-ethyl-1-hexanol in the presence of titanium (IV) isopropoxide as catalyst. However, the prior art processes for recovering the product have been unsatisfactory because of residual acidity in the reaction product and the presence of insoluble titanium catalyst residue. For example, Spatz, et al., "Discoloration of Tetrabromophthalic Anhydride Polyester Resins." I&EC Product Research and Development. Volume 8, December, 1969, pages 391, 395. describe two variations in the recovery of bis(2-ethyl-1-hexyl) tetrabromophthalate obtained by acid catalyzed esterification of tetrabromophthalic anhydride. The authors first suggest using low pressure distillation to recover the product after an elaborate purification by washing. Alternatively, the use of column chromotography is described. However. neither technique appears to be totally effective or commercially practicable.

Japanese Pat No. 50/5701. issued Mar. 6, 1975. describes a product purification approach involving the removal of excess alcohol in vacuo. followed by treatment of the crude ester with activated clay. Again, the reported results did not yield levels of satisfactory product quality.

U.S. Pat. No. 4,214.103 describes the purification of crude halogenated products. especially nuclear halogenated products produced by contacting an excess of bromine with the aromatic compound such as diphenyl ether in the presence of a bromination catalyst such as iron. aluminum and their halides. The described process comprises contacting the crude nuclear halogenated product with a finely divided basic solid such as a carbonate or bicarbonate of an alkali metal or ammonia in an organic solvent or in a molten state in the presence of a small amount of water. While the described process was successful in achieving its objectives. it did not deal with the problems posed by the recovery of bis(2-ethyl-1-hexyl) tetrabromophthalate, that is, the necessity of reducing residual acidity and removing titanium containing catalyst residue.

Accordingly. a primary object of the present invention is to provide a process for recovery of alkyl tetrabromophthalates.

A related object is to provide a method for recovery of bis(2-ethyl-1-hexyl) tetrabromophthalate produced by the reaction of tetrabromophthalic anhydride and 2-ethyl-1-hexanol in the presence of titanium isopropoxide catalyst.

A still further object is to provide a method of recovering bis(2-ethyl-1-hexyl) tetrabromophthalate which reduces residual acidity in the finished product to a very low level and which converts the titanium containing catalyst residue to a form that can be separated from the reaction product by filtration or other physical means.

SUMMARY OF THE INVENTION

The foregoing and other objects. advantages and features of the present invention may be achieved with a method for recovering alkyl tetrabromophthalate obtained by reacting tetrabromophthalic anhydride with an alkanol in the presence of titanium lower alkoxide catalyst. The method comprises the steps of contacting the reaction mixture with a effective amount of sodium carbonate decahydrate with agitation for time and at a temperature sufficient to enhance the quality of the product; and isolating alkyl tetrabromophthalate from the reaction mixture. Effectiveness of the product recovery techniques of this invention are optimized by conducting the initial treatment with sodium carbonate in a closed system in the presence of a small but effective quantity of water supplied by the sodium carbonate decahydrate, with that water being removed before the product is isolated.

DETAILED DESCRIPTION OF THE PREFERRED EMBODIMENTS

The process of producing alkyl tetrabromophthalate by reacting tetrabromophthalic anhydride with an alkanol in the presence of titanium lower alkoxide catalyst is well known in the art. The product produced by the foregoing reaction, however. generally exhibits an undesirably high level of acidity (e.g., 3 meq./100 grams or more). Moreover. the titanium catalyst residue exists in a soluble form in the reaction mixture and is difficult to separate from the product.

In general, tetrabromophthalic anhydride is reacted with alkanol in the presence of titanium lower alkoxide catalyst in any suitable reaction vessel. The reaction preferably is conducted under a nitrogen atmosphere.

The alkanol reacted in accordance with this invention may be a $C_{1-18}$ alkanol, preferably a $C_{4-16}$ alkanol. Especially preferred alkanols in accordance with this invention include 2-ethyl-1-hexanol and mixtures of $C_{6-10}$ alcohols, especially mixtures of hexyl, octyl and decyl alcohols.

The titanium lower alkoxide catalyst may be a titanium $C_{2-4}$ alkoxide such as the ethoxide. propoxides. and butoxides of titanium (IV). Titanium isopropoxide is especially preferred.

Products produced by the foregoing reaction are $C_{1-18}$ alkyl tetrabromophthalates. Preferred products include $C_{1-16}$ alkyl tetrabromophthalates. Bis(2-ethyl-1-hexyl) tetrabromophthalate, obtained from the reaction of 2-ethyl-1-hexanol with tetrabromophthalic anhydride, is an especially preferred product in accordance with this invention. Mixture of hexyl, octyl, and decyl tetrabromophthalates are also preferred in accordance herewith.

An excess of alkanol is desirably employed as is well known to those skilled in the art (e.g., about 5-100 percent. based on tetrabromophthalic anhydride). The amount of titanium lower alkoxide catalyst is also maintained within known limits (generally about 0.05-5.0 volume percent based on tetrabromophthalic anhydride). Preferably, about 50 percent excess alkanol and about 0.5 volume percent titanium lower alkoxide are employed.

It has been found that the desired recovery objectives may simply and easily be met by treating the crude alkyl tetrabromophthalate reaction mixture with crystalline sodium carbonate decahydrate with agitation at elevated temperatures. Desirably, the initial stage of the recovery process is carried out in a closed system in the presence of a small but effective amount of water supplied by the water of hydration of sodium carbonate decahydrate. The process of the present invention reduces the original acidity to a very low level and, additionally, causes precipitation of the titanium catalyst residue so that it can be separated by filtration during product isolation.

The crystalline sodium carbonate decahydrate may conveniently be added to the reaction mixture in the product reactor or other convenient vessel following the conclusion of the esterification reaction. Substantially any effective amount of sodium carbonate decahydrate may be added in order to achieve the benefits of the present invention. Preferably about 0.1–20 percent sodium carbonate decahydrate, by weight of the reaction mixture is employed. It is especially preferred to employ about 5 weight percent sodium carbonate decahydrate by weight of the reaction mixture.

Alternatively, the sodium carbonate decahydrate may be supplied in the form of anhydrous sodium carbonate in combination with that amount of water corresponding to the decahydrate (i.e., 10 moles of water per mole of anhydrous sodium carbonate). For example, about 1.7 liters water is added per kilogram of anhydrous sodium carbonate utilized in accordance with this invention.

The reaction mixture containing the sodium carbonate decahydrate is agitated at elevated temperature. Desirably, the reaction mixture is maintained at a temperature in the range of about 30°–120° C. A temperature of about 90° C. is especially preferred.

The reaction mixture containing sodium carbonate is agitated at elevated temperature for a period of time sufficient to effect the desired quality improvement. Desirably, the agitation continues for about 0.5–1 hours, although shorter or longer times may be employed as long as acidity is reduced to satisfactory levels and catalyst residues are separated from the product after the remaining water is removed.

Alkyl tetrabromophthalate is then isolated from the mixture, which is filtered to separate catalyst residues and other undesirable materials.

One preferred method of product isolation involves passing a stream of air above the reaction mixture while subjecting it to additional heating to a temperature in the range of about 100°–150° C., preferably about 130° C., for about 0.5–1 hours in order to remove the water provided by the sodium carbonate decahydrate. After the water has been removed, the product can be cooled and filtered in order to separate catalyst residue and other impurities from the purified product, and stripped in order to remove the unreacted alcohol.

Alternatively, the product may also be isolated by passing steam through the liquid reaction mixture and collecting a two-layer distillate of aqueous and organic phases, followed by removal of the residual water by azeotropic distillation up to about 130° C. The product may again be further treated by filtration.

EXAMPLES

Example 1

Preparation of Bis(2-ethyl-1-hexyl) Tetrabromophthalate

Tetrabromophthalic anhydride (1391.1 grams; 3.0 moles), 2-ethyl-1-hexanol (1171.8 grams; 9.0 moles) and titanium (IV) isopropoxide (7 ml.; 0.5 volume percent on tetrabromophthalic anhydride) were charged into a 3,000 ml. reaction flask maintained under a nitrogen atmosphere. The reaction flask was fitted with a mechanical stirrer, thermometer, nitrogen inlet tube, and a Dean-Stark water trap connected to a Friedrich condensor. The reaction mixture was heated with agitation at a temperature equal or less than about 200° C. for eight hours. The resulting product (2.497 grams) was an amber thick clear liquid having an acidity of 1.4 meq. per 100 grams.

Example 2

Recovery of Bis(2-ethyl-1-hexyl) Tetrabromophthalate

The reaction mixture from Example 1 was cooled to approximately 90° C. and the Dean-Stark water trap was removed and replaced with a reflux condenser. Nitrogen flow was shut off, and sodium carbonate decahydrate crystal (124.grams, 5 weight percent by weight on the reaction mixture) was added to the reaction mixture with efficient agitation at about 90° C. for about 0.5 hours.

The bis(2-ethyl-1-hexyl) tetrabromophthalate was isolated from the reaction mixture, which contained some unreacted 2-ethyl-1-hexanol, by steam distillation of the alcohol, followed by nitrogen purge at 130° C. and filtration of the purged residue at about 110°–115° C.

Product yield from filtration was 2030.0 grams, about 95.9 percent based on the tetrabromophthalic anhydride starting material. Additional quantities of high quality bis(2-ethyl-1-hexyl) tetrabromophthalate may be isolated from the spent sodium carbonate filtration residue and thus permitting a total yield of 2105.6 grams, 99.4 percent based on the tetrabromophthalic anhydride starting material. Properties of the isolated bis(2-ethyl-1-hexyl) tetrabromophthalate product are given in Table I.

TABLE I

| Product Properties | |
|---|---|
| Appearance: | Gold, clear thick liquid |
| Br (calcd. 45.3%): | 44.8% |
| Acidity: | ≦0.01 meq./100 g. |
| Ash: | 0.04% |
| VPC Assay: | 0.43 area % |
| 2-ethyl-1-hexanol: | |
| Tetrabromophthalic anhydride | 0.04 area % |
| Bis(2-ethyl-1-hexyl)-tetrabromo phthalate | 92.9 |

Example 3

Comparative Example

A series of recovery runs were conducted in order to evaluate the efficacy of a variety of purification agents. The agents were either used "neat," that is, the agents were added to the crude bis(2-ethyl-1-hexyl) tetrabromophthalate reaction mixture, or they were added to the crude product provided in an organic solvent (methylene chloride or toluene). The bis(2-ethyl-1-hexyl) tetrabromophthalate product was recovered from the treated mixture by filtration and/or by stripping. The results given in Table II.

TABLE II

| Purification Agent | Acidity (meq/100 g.) |
|---|---|
| None | 2.65 |
| Na$_2$CO$_3$.H$_2$O | ≦0.001 |

TABLE II-continued

| Purification Agent | Acidity (meq/100 g.) |
|---|---|
| $Na_2CO_3.H_2O$ (open/closed) | 0.774 |
| $Na_2CO_3.10H_2O$ (closed/open) | $\leq 0.001$ |
| $Na_2CO_3$ | 1.53 |
| CaO | 0.23 |
| $CaCO_3$ | 2.70 |
| Propylene Oxide | 0.44 |
| $NH_4OH$ | 2.08 |
| $NH_2NH_2.H_2O$ | 0.27 |
| $H_2O_2$ | 2.79 |
| Activated Carbon | 2.29 |
| Tonsil Clay | 2.64 |
| Attapulgus Clay | 2.45 |
| $NH_3$ (gas) | 0.98 |
| $CO_2$ | 2.57 |
| Std. Washing | 0.014 |
| $Na_2CO_3$ in Toluene | 0.56 |
| $Na_2CO_3.H_2O$ in Toluene | 1.16 |
| $Na_2CO_3.10H_2O$ in Toluene | $\leq 0.005$ |

The data in Table II demonstrate that use of an organic solvent to aid in recovery is not advantageous. In addition, of all of the agents tested. only sodium carbonate decahydrate and sodium carbonate monohydrate produced a product with the desired low level of acidity. In addition. sodium carbonate decahydrate is significantly more effective than sodium carbonate monohydrate because the reaction mixture filters faster when the decahydrate is used.

Thus. recovery of bis(2-ethyl-1-hexyl) tetrabromophthalate using the process of the present invention is the only approach that permits the desired level of neutralization of residual acidity to be achieved, that converts the titanium catalyst residue from soluble to insoluble form which may be removed by filtration, and that results in easy and fast filtration.

We claim:

1. A process for recovery of an alkyl tetrabromophthalate produced by reaction of tetrabromophthalic anhydride with a $C_{1-18}$ alkanol in the presence of titanium lower alkoxide catalyst comprising the steps of:
   contacting the reaction mixture with an effective amount of sodium carbonate decahydrate with agitation for a time and at a temperature sufficient to enhance the quality of the product; and
   isolating alkyl tetrabromophthalate from the reaction mixture.

2. A process. as claimed in claim 1, wherein about 0.1–20 percent by weight sodium carbonate decahydrate is utilized based on the weight of the reaction mixture.

3. A process. as claimed in claim 2, wherein about 5 percent by weight sodium carbonate decahydrate is utilized.

4. A process. as claimed in claim 1, wherein the the reaction mixture is contacted with sodium carbonate decahydrate with agitation for about 0.5–1 hours.

5. A process. as claimed in claim 4, wherein the reaction mixture is maintained in a closed system after sodium carbonate decahydrate addition.

6. A process. as claimed in claim 1, wherein the alkyl tetrabromophthalate is isolated from the reaction mixture by first removing water and unreacted alkanol therefrom and thereafter filtering the product.

7. A process as claimed in claim 6, wherein the water is removed by application of heat in the presence of a flow of unreactive gas.

8. A process. as claimed in claim 6, wherein the unreacted alkanol is removed by steam distillation.

9. A process. as claimed in claim 6, wherein the water and unreacted alkanol are removed by azeotropic distillation.

10. A process. as claimed in claim 1, wherein sodium carbonate decahydrate is provided by the separate addition of anhydrous sodium carbonate and the corresponding amount of water necessary to provide about ten moles of water per mole of anhydrous sodium carbonate.

11. A process. as claimed in claim 1, wherein the catalyst is titanium isopropoxide.

12. A process. as claimed in claim 1, wherein the alkanol is 2-ethyl-1-hexanol.

13. A process. as claimed in claim 1, wherein the alkanol is a mixture of hexyl, octyl. and decyl alcohols.

14. A process for recovery of bis(2-ethyl-1-hexyl) tetrabromophthalate produced by the reaction of tetrabromophthalic anhydride with 2-ethyl-1-hexanol in the presence of titanium isopropoxide catalyst comprising the steps of:
   contacting the reaction-mixture with about 0.1–20 percent sodium carbonate decahydrate, by weight of the reaction mixture, at a temperature of about 30°–120° C. for a time sufficient to enhance the quality of the product; and
   isolating bis(2-ethyl-1-hexyl) tetrabromophthalate from the reaction mixture.

* * * * *

UNITED STATES PATENT AND TRADEMARK OFFICE
CERTIFICATE OF CORRECTION

PATENT NO. : 4,754,053                                Page 1 of 5

DATED     : June 28, 1988

INVENTOR(S) : Rastko I. Mamuzic and Bhabatosh Bhattacharya

It is certified that error appears in the above—identified patent and that said Letters Patent is hereby corrected as shown below:

BACKGROUND OF THE INVENTION

Column 1, line 22 "Resins." should be "Resins,"

Column 1, line 22 "Development." should be "Development,"

Column 1, line 23 "395." should be "395,"

Column 1, line 30 "However." should be "However,"

Column 1, line 32 "50/5701." should be "50/5701,"

Column 1, line 32 "1975." should be "1975,"

Column 1, line 34 "vacao." should be "vacao,"

Column 1, line 38 "4,214.103" should be "4,214,103"

Column 1, line 39 "products." should be "products,"

Column 1, line 43 "iron." should be "iron,"

Column 1, line 49 "objectives." should be "objectives,"

Column 1, line 54 "Accordingly." should be "Accordingly,"

SUMMARY OF THE INVENTION

Column 2, line 3 "objects." should be "objects,"

UNITED STATES PATENT AND TRADEMARK OFFICE
CERTIFICATE OF CORRECTION

PATENT NO. : 4,754,053
DATED : June 28, 1988
INVENTOR(S) : Rastko I. Mamuzic and Bhabatosh Bhattacharya It is certified that error appears in the above—identified patent and that said Letters Patent is hereby corrected as shown below:

Column 2, line 9 "a" should be "an"

DETAILED DESCRIPTION OF THE PREFERRED EMBODIMENTS

Column 2, line 27 "however." should be "however,"

Column 2, line 29 "Moreover." should be "Moreover,"

Column 2, line 43 "ethoxide. propoxides." should be "ethoxide, propoxides,

Column 2, line 57 "percent." should be "percent,"

Column 3, line 16 "decahydrate." should be "decahydrate,"

Column 3, line 17 "mixture" should be "mixture,"

Column 3, line 20 "Alternatively." should be "Alternatively,"

Column 3, line 24 "example." should be "example,"

Column 3, line 31 "120° C." should be "120°C."

Column 3, line 32 "90° C." should be "90°C"

Column 3, line 36 "Desirably." should be "Desirably,"

Column 3, line 41 "mixture." should be "mixture,"

UNITED STATES PATENT AND TRADEMARK OFFICE
CERTIFICATE OF CORRECTION

PATENT NO. : 4,754,053

DATED : June 28, 1988

INVENTOR(S) : Rastko I. Mamuzic and Bhabatosh Bhattacharya

It is certified that error appears in the above-identified patent and that said Letters Patent is hereby corrected as shown below:

Column 3, line 46 "-150° C.," should be "-150°C,"

Column 3, line 47 "C.," should be "C,"

Column 3, line 49 "removed." should be "removed,"

Column 3, line 57 "130° C" should be "130°C"

Example 1

Column 4, line 3 "stirrer. thermometer." should be "stirrer, thermometer,"

Column 4, line 6 "200° C" should be "200°C"

Column 4, line 7 "2.497" should be "2,497"

Example 2

Column 4, line 15 "90° C" should be "90°C"

Column 4, line 18 "124." should be "124.9"

Column 4, line 20 "90° C." should be "90°C"

Column 4, line 23 "mixture." should be "mixture,"

UNITED STATES PATENT AND TRADEMARK OFFICE
CERTIFICATE OF CORRECTION

PATENT NO. : 4,754,053
DATED : June 28, 1988
INVENTOR(S) : Rastko I. Mamuzic and Bhabatosh Bhattacharya It is certified that error appears in the above—identified patent and that said Letters Patent is hereby corrected as shown below:

Column 4, line 25 "130° C" should be "130°C"

Column 4, line 26 "110°-115°" should be "110°-"

Column 4, line 27 "C." should be "115°C."

Example 3

Column 5, line 22 "tested." should be "tested,"

Column 5, line 25 "addition." should be "addition,"

Column 5, line 29 "Thus." should be "Thus,"

IN THE CLAIMS

Claim 2, line 47 "process." should be "process,"

Claim 3, line 3 "process." should be "process,"

Claim 4, line 6 "process." should be "process,"

Claim 4, line 6 delete second "the"

Claim 5, line 9 "process." should be "process,"

UNITED STATES PATENT AND TRADEMARK OFFICE
CERTIFICATE OF CORRECTION

PATENT NO. : 4,754,053
DATED : June 28, 1988
INVENTOR(S) : Rastko I. Mamuzic and Bhabatosh Bhattacharya It is certified that error appears in the above—identified patent and that said Letters Patent is hereby corrected as shown below:

Claim 6, line 12 "process." should be "process,"

Claim 8, line 19 "process." should be "process,"

Claim 9, line 21 "process." should be "process,"

Claim 10, line 24 "process." should be "process,"

Claim 11, line 30 "process." should be "process,"

Claim 12, line 32 "process." should be "process,"

Claim 13, line 34 "process." should be "process,"

Claim 13, line 35 "octyl." should be "octyl,"

Claim 14, line 44 "-120° C." should be "-120°C"

Signed and Sealed this

Fourteenth Day of February, 1989

*Attest:*

DONALD J. QUIGG

*Attesting Officer*  *Commissioner of Patents and Trademarks*